United States Patent
Townes et al.

(10) Patent No.: US 6,306,650 B1
(45) Date of Patent: *Oct. 23, 2001

(54) NUCLEIC ACID MOLECULE ENCODING A β-ERYTHROID KRÜ PPEL-LIKE FACTOR THAT BINDS TO A δ-GLOBIN PROMOTER

(75) Inventors: Tim M. Townes, Birmingham, AL (US); David Donze, Silver Spring, MD (US)

(73) Assignee: UAB Research Foundation, Birmingham, AL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/874,569

(22) Filed: Jun. 13, 1997

Related U.S. Application Data

(60) Provisional application No. 60/019,769, filed on Jun. 14, 1996.

(51) Int. Cl.$^7$ ............................ C12N 5/10; C12N 1/00; C12N 15/63; C07H 21/04
(52) U.S. Cl. .................. 435/325; 435/243; 435/320.1; 435/410; 536/23.5
(58) Field of Search ................. 536/23.1, 23.5; 435/325, 410, 243, 320.1

(56) References Cited

U.S. PATENT DOCUMENTS 5,789,538 * 8/1998 Rebar et al. .

OTHER PUBLICATIONS

Ngo et al, The Protein Folding Problem and Tertiary Structure Prediction, Merts et al (eds.), Birkhauser, Boston, pp. 433 and 492–495, 1994.*

Cowie et al., "DNA Sequences Involved in Transcriptional Regulation of the Mouse β–Globin Promoter in Murine Erythroleukemia Cells," Mol. Cell. Biol. 8:3122 (1988).

Dierks et al., "Three Regions Upstream from the Cap Site Are Required for Efficient And Accurate Transcription of the Rabbit β–Globin Gene in Mouse 3T6 Cells," Cell 32:695 (1983).

Myers et al., "Fine Structure Genetic Analysis of a β–Globin Promoter," Science 232:613 (1986).

Nagel et al., "Structure Bases of the Inhibitory Effects of Hemoglobin F and Hemoglobin $A_2$ on the Polymerization of Hemoglobin S," Proc. Natl. Acad. Sci USA 76:670 (1979).

Steinberg et al., "Hemoglobin $A_2$: Origin, Evolution,and Aftermath," Blood 78:2165 (1991).

Bieker, "Isolation, Genomic Structure, and Expression of Human Erythroid Kruppel–Like Factor (EKLF)," DNA and Cell Biology 15:347–352 (1996).

Miller and Bieker, "A Novel, Erythroid Cell–Specific Murine Transcription Factor That Binds to the CACCC Element and is Related to the Kruppel Family of Nuclear Proteins," Molecular and Cellular Biology 13:2776–2786 (1993).

Gregory et al., "Functional Interaction of GATA1 With Erythroid Kruppel–Like Factor and SP1 at Defined Erythroid Promoters," Blood 87:1793–1801 (1996).

Perkins et al., "Lethal β–Thalassaemia in Mice Lacking the Erythroid CACCC–Transcription Factor EKLF," Nature 375:318–322 (1995).

Nuez et al., "Defective Haematopoiesis in Fetal Liver Resulting from Inactivation of the EKLF Gene," Nature 375:316–318 (1995).

Donze et al., "Role of Erythroid Kruppel–Like Factor in Human γ– to β–Globin Gene Switching," Journal of Biological Chemistry 270:1955–1959 (1995).

Bieker and Southwood, "The Erythroid Kruppel–Like Factor Transactivation Domain is a Critical Component for Cell–Specific Inducibility of a β–Globin Promoter," Molecular and Cellular Biology 15:852–860 (1995).

Feng et al., "Analyses of β–Thalassemia Mutant DNA Interactions with Erythroid Kruppel–Like Factor (EKLF), and Erythroid Cell–Specific Transcription Factor," Journal of Biological Chemistry 269:1493–1500 (1994).

Merika and Orkin, "Functional Synergy and Physical Interactions of the Erythroid Transcription Factor GATA–1 with the Kruppel Family Proteins Sp1 and EKLF," Molecular and Cellular Biology 15:2437–2447 (1995).

Tang et al., "Restoration of the CCAAT Box or Insertion of the CACCC Motif Activate δ–Globin Gene Expression," Blood 90:421–427 (1997).

Donze et al., "Activation of δ–Globin Gene Expression by Erythroid Kruppel–Like Factor: A Potential Approach for Gene Therapy of Sickle Cell Disease," Blood 88:4051–4057 (1996).

* cited by examiner

*Primary Examiner*—Terry McKelvey
(74) *Attorney, Agent, or Firm*—Needle & Rosenberg, P.C.

(57) ABSTRACT

The invention features δ-erythroid krüppel-like factors (δ-EKLFs), and methods of using nucleic acids encoding δ-EKLFs to increase δ-globin gene expression in a cell.

10 Claims, 9 Drawing Sheets

(SEQ ID NO: 10)   β         TGTGGAGCCACACCCTAGGGTTGGCCAATCTACTCCC
                                    |          |
                                   −93        −85

(SEQ ID NO: 11)   δ         TCACAAACTAATGAAACCCTGCTTATCTTAAACCAAC
                                            |   |
                                           −85 −81

(SEQ ID NO: 12)   δ^CAC-1   TCACAAACTAACCACACCCTGCTTATCTTAAACCAAC
                                       |        |
                                      −89      −81

(SEQ ID NO: 13)   δ^CAC-2   TCACAAACCACACCCTCCCTGCTTATCTTAAACCAAC
                                   |        |
                                  −93      −85

FIG.1B

```
             -1 23456
FINGER 1    CGHEGCGKSYSKSSHLKAHLRTH  (SEQ ID NO: 14)

-1 23456
FINGER 2    CSWDGCDWRFARSDELTRHYRKH  (SEQ ID NO: 15)

-1 23456
FINGER 3    CGLCGLCPRAFSRSDHLALHMKRH (SEQ ID NO: 16)
```

FIG.2

NUCLEIC ACID MOLECULE ENCODING A β-ERYTHROID KRÜPPEL-LIKE FACTOR THAT BINDS TO A δ-GLOBIN PROMOTER

CROSS REFERENCE TO RELATED APPLICATION

This application claims benefit from provisional application Ser. No. 60/019,769, which was filed on Jun. 14, 1996.

BACKGROUND OF THE INVENTION

This invention relates to gene therapy methods for treating hemoglobinopathies.

The major form of adult human hemoglobin, HbA, consists of a tetramer of two α-globin chains and two β-globin chains ($\alpha_2\beta_2$). Hemoglobinopathies, such as sickle cell anemia and $\beta^0$-thalassemia, are caused by a failure to produce normal levels of β-globin. Hemoglobin $A_2$ (Hb$A_2$), which consists of a tetramer of two α-globin chains and two β-globin chains ($\alpha_2\delta_2$), is produced in low amounts in most sickle cell patients and in normal adults (2–3% of total hemoglobin) (Steinberg et al., Blood 78:2165, 1991). Hb$A_2$ is a potent inhibitor of the sickle hemoglobin (HbS; $\alpha_2\beta^s_2$) polymerization characteristic of sickle cell anemia (Nagel et al., Proc. Natl. Acad. Sci. USA 76:670, 1979), and shares some functional activity with HbA.

SUMMARY OF THE INVENTION

We have shown that modification of the δ-globin gene promoter to include a binding site for the erythroid krüppel-like factor (EKLF) polypeptide that binds to the β-globin gene promoter (hereinafter "β-EKLF") results in increased expression from the δ-globin promoter. A modified β-EKLF (hereinafter "δ-EKLF") that binds to the wild type δ-globin gene promoter can thus be used to induce δ-globin expression.

Accordingly, in one aspect, the invention features a method of inducing δ-globin gene expression in a cell, such as an erythrocyte precursor cell (e.g., an erythrocyte burst-forming cell (BFC-E) or an erythrocyte colony-forming cell (CFC-E)) or an erythrocyte. In this method, a nucleic acid encoding a δ-EKLF polypeptide is introduced into the cell, or a precursor of the cell. Cells into which the nucleic acid can be introduced include erythrocyte precursors, such as BFC-E and CFC-E. Preferably, the nucleic acid is introduced into a pluripotent hematopoietic stem cell, which is capable of self renewal, and thus, in the context of gene therapy methods (see below), minimizes the number of treatments required.

The cell into which the nucleic acid is introduced can be in a mammal or can be a cell that has been removed from a mammal for introduction of the nucleic acid, after which the cell, or progeny thereof, are introduced into a mammal. Typically, this method is carried out for a human patient. In one particular example, the nucleic acid can be introduced into a hematopoietic stem cell that has been obtained from a patient. Induction of δ-globin gene expression by this method can be used in gene therapy methods for the treatment of hemoglobinopathies, such as sickle cell anemia and $\beta^0$-thalassemia.

The invention also features δ-EKLF polypeptides, which are identical to β-EKLF, except that they contain one or more modifications that permit them to bind to double stranded DNA containing the sequence 5'-TGA AAC CCT-3' or the sequence 5'-CTA ATG AAA-3'. The modifications that generate δ-EKLF polypeptides are generally in a DNA-binding amino acid of a zinc finger of the β-EKLF polypeptide. For example, modifications can be made in any of amino acids −1 and/or 2–6 in any of the three β-EKLF zinc fingers (see below and FIG. 2).

Preferably, the δ-EKLF polypeptide of the invention is in a substantially pure preparation. By "substantially pure" is meant a preparation that is at least 60% by weight (dry weight) a δ-EKLF polypeptide. Preferably the preparation is at least 75%, more preferably at least 90%, and most preferably at least 99%, by weight a δ-EKLF polypeptide. Purity can be measured by any appropriate method, e.g., column chromatography, polyacrylamide gel electrophoresis, or HPLC analysis.

Also featured in the invention is a nucleic acid, such as a nucleic acid containing deoxyribonucleotides (DNA), ribonucleotides (RNA), or combinations or modifications thereof, encoding δ-EKLF polypeptides. Preferably, the nucleic acid is in the form of purified DNA. By "purified DNA" is meant DNA that is not immediately contiguous with both of the coding sequences with which it is immediately contiguous (one on the 5' end and one on the 3' end) in the naturally occurring genome of the organism from which it is derived. The term thus includes, for example, a recombinant DNA molecule that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA molecule that is part of a hybrid gene encoding additional polypeptide sequence.

The invention also includes cells, such as hematopoietic stem cells or erythrocyte precursor cells, e.g., BFC-E or CFC-E, that contain nucleic acids encoding δ-EKLF polypeptides.

Vectors containing nucleic acids encoding δ-EKLF polypeptides are also included in the invention. The vectors of the invention include those that can be used in gene therapy methods for treating hemoglobinopathies, such as sickle cell anemia and $\beta^0$-thalassemia. For example, adeno-associated viral (AAV) vectors and retroviral vectors (e.g., moloney murine leukemia viral vectors) can be used in the invention. Vectors that can be used for amplifying nucleic acids encoding δ-EKLF polypeptides in bacteria are also included in the invention. Preferably, the nucleic acids encoding δ-EKLF polypeptides are operably linked to a promoter, for example, the β-globin promoter, or a non-tissue specific promoter, such as the Cytomegalovirus promoter. By "operably linked" is meant that a gene and a regulatory sequence(s), such as a promoter, are connected in such a way as to permit gene expression when the appropriate molecules (e.g., transcriptional activator proteins or proteins which include transcriptional activation domains) are bound to the regulatory sequence(s).

The invention also features methods for identifying δ-EKLF polypeptides. In these methods, a nucleic acid containing either the sequence 5'-TGA AAC CCT-3' or the sequence 5'-CTA ATG AAA-3' is contacted with a candidate polypeptide that has been modified such that it differs from wild type β-EKLF by at least one amino acid, for example, an amino acid in a β-EKLF zinc finger that binds DNA. δ-EKLF polypeptides are then identified by their ability to bind to this nucleotide sequence.

Expression of therapeutic levels of gene products in gene therapy methods is often difficult to achieve. Transcription factors are generally required in lower quantities than other types of therapeutic gene products. Thus, an advantage of the present invention is that it provides a gene therapy method involving expression of a transcription factor, δ-EKLF.

Other features and advantages of the invention will be apparent from the following detailed description, the drawings, and the claims.

BRIEF DESCRIPTION OF THE DRAWINGS

FIG. 1B is a schematic representation of a comparison of portions of the human δ- and β-globin promoters, and modifications of the δ-globin promoter to contain β-EKLF binding sites. The β- and δ-globin promoters were aligned using the GAP program of the GCG/Wisconsin package, and the regions of interest are shown (β:SEQ ID NO:10; δ: SEQ ID NO:11). The consensus β-EKLF binding site in the β-globin promoter (CCACACCCT) is located at nucleotide positions −85 to −93 from the transcription start site and this sequence is underlined. The wild type δ-globin promoter region has a partial EKLF binding site (ACCCT) at nucleotide positions −81 to −85. To create the modified $\delta^{CAC-1}$ promoter (SEQ ID NO:12), site-directed mutagenesis was used to convert the partial β-EKLF binding site in the δ-globin promoter to a consensus β-EKLF binding site. The $\delta^{CAC-2}$ promoter (SEQ ID NO:13) contains the β-globin EKLF binding site at nucleotide positions −85 to −93 of the δ-globin promoter, which is at the same distance from the transcription start site as the β-globin promoter EKLF binding site.

FIG. 2 is a schematic representation of the amino acid sequences of β-EKLF zinc fingers 1 SEQ ID NO:14), 2 SEQ ID NO:15), and 3 SEQ ID NO:16). Amino acids that can be randomized for selecting δ-globin promoter binding variants include those that are boxed.

DETAILED DESCRIPTION

As discussed above, the major form of adult human hemoglobin, HbA, consists of a tetramer of two α-globin chains and two β-globin chains (α$_2$β$_2$) Hemoglobinopathies, such as sickle cell anemia and β$^0$-thalassemia, are caused by a failure of erythrocytes and erythrocyte precursors to produce normal levels of β-globin. Also as discussed above, hemoglobin A$_2$ (HbA$_2$), which consists of a tetramer of two α-globin chains and two δ-globin chains (α$_2$δ$_2$), is produced in low amounts in most sickle cell patients and normal adults (2–3% of total hemoglobin). HbA$_2$ has potent anti-sickling activity and shares some functional activity with HbA. Thus, induction of increased levels of δ-globin, in order to facilitate generation of increased levels of HbA$_2$, can be used to treat hemoglobinopathies, such as sickle cell anemia and β$^0$ thalassemia.

The CACCC box at nucleotide positions −93 to −85 in the β-globin gene promoter is important for β-globin gene expression (Dierks et al., Cell 32:695, 1983; Myers et al., Science 232:613, 1986; Cowie et al., Mol. Cell. Biol. 8:3122, 1988). The major protein that binds to the CACCC box of the β-globin promoter is the erythroid-specific, zinc finger transcription factor EKLF (Miller et al., Mol. Cell. Biol. 13:2776, 1993). β-EKLF contains three zinc fingers, which bind to the successive DNA base triplets, 5'-CCA CAC CCC-3' (nucleotides −93 to −85 with respect to the β-globin gene transcription start site), of the β-globin CACCC box. In conjunction with proteins bound to the locus control region (LCR), EKLF binding to the β-globin CACCC box activates high levels of β-globin gene expression (Donze et al., J. Biol. Chem. 270:1955, 1995; Nuez et al., Nature 375:316, 1995; Perkins et al., Nature 375:318, 1995).

Figure 1A:
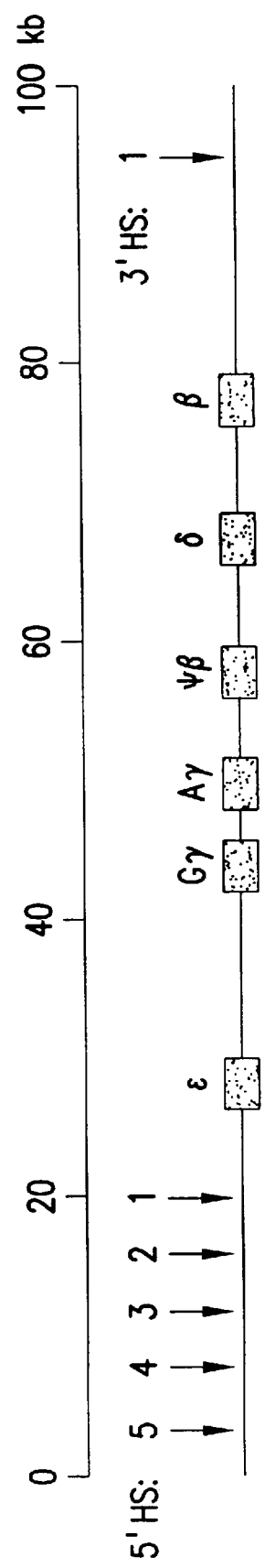
FIG. 1A is a schematic representation of the β-globin locus on human chromosome 11.

The human δ- and β-globin genes are located at the 3' end of the β-globin locus on chromosome 11 (FIG. 1A). Comparison of the sequences of the δ- and β-globin proximal promoters (FIG. 1B) reveals that the δ-globin promoter lacks consensus CACCC and CCAAT boxes, which are present in the β-globin promoter and are important for adult β-globin gene expression (Dierks et al., Cell 32:695, 1983; Myers et al., Science 232:613, 1986; Cowie et al., Mol. Cell. Biol. 8:3122, 1988).

Sequence comparisons and analyses of crystal structures of other zinc finger-containing proteins bound to their DNA binding sites have revealed that amino acid positions in zinc finger α-helices that are involved in nucleotide-specific contacts are conserved. These conserved positions have been designated −1, 2, 3, and 6, with respect to the beginning of the α-helix, and are shown for each β-EKLF zinc finger in FIG. 2. Positions 4 and 5 may also affect sequence-specific DNA recognition.

Figure 6:
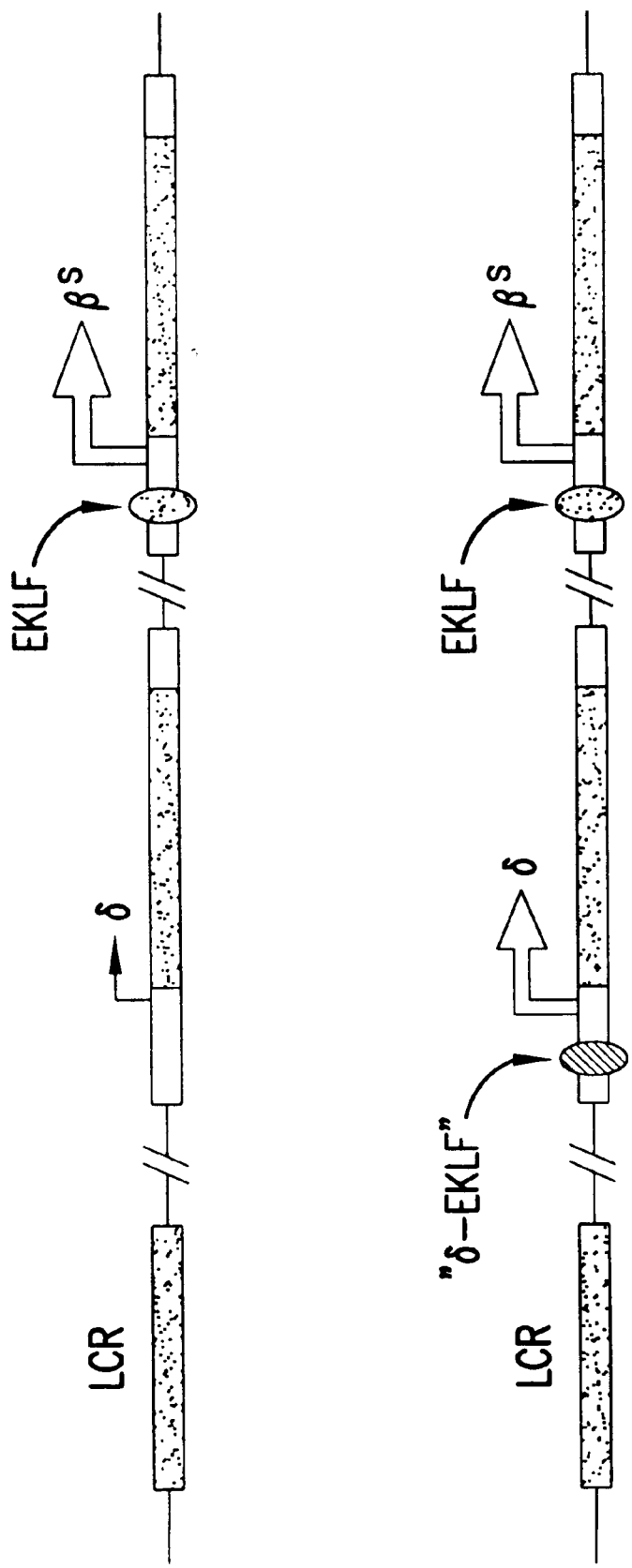
FIG. 6 is a schematic representation of a model of δ-EKLF activation of δ-globin gene expression. The δ-globin gene is normally expressed at a low level in erythroid cells. One reason for low δ-globin expression is the defective CACCC box at −90 in the δ-globin gene promoter. A modified β-EKLF, δ-EKLF, which contains zinc fingers designed to bind specifically to the defective δ-globin CACCC box, can be used in gene therapy approaches to increase RbA$_2$ levels and inhibit erythrocyte sickling.

The δ-globin gene promoter contains a partial β-EKLF binding site, 5'-TGA AAC CCT-3', at nucleotide positions −89 to −81. β-EKLF does not bind to the δ-globin partial β-EKLF binding site. As is described further below, insertion of a β-EKLF binding site into the δ-globin promoter, at or near the δ-globin partial β-EKLF binding site, enhances expression from the δ-globin promoter. Thus, modified β-EKLFs, which bind to δ-globin promoter sequences at or near the partial β-EKLF binding site and enhance transcription from the δ-globin promoter, can be used in methods to increase δ-globin expression (FIG. 6).

The invention provides modified β-EKLFs, designated δ-EKLFs, that contain altered zinc finger sequences that bind to, and enhance expression from, the δ-globin promoter. δ-EKLFs of the invention bind to, for example, nucleic acids containing the partial β-globin EKLF binding site (5'-TGA AAC CCT-3') of the δ-globin promoter. Also included in the invention are δ-EKLFs that bind to nucleic acids containing δ-globin nucleotides −93 to −85, which are at the same position in the δ-globin promoter, relative to the transcription start site, as the β-EKLF binding site in the β-globin promoter. Genes that encode δ-EKLFs can be used in gene therapy methods for increasing $HbA_2$ production, which is useful in the treatment of hemoglobinopathies, such as sickle cell anemia and $β^0$-thalassemia.

Production of δ-EKLFs

δ-EKLFs can be isolated, for example, using the phage display method (see, e.g., Rebar et al., Science 263:671, 1994; Smith, Science 228:1315, 1985; Wu et al., Proc. Natl. Acad. Sci. USA 92:344, 1995; Jamieson et al., Biochemistry 33:5689, 1994; Choo et al., Nature 372:642, 1994; Choo et al., Proc. Natl. Acad. Sci. USA 91:11163, 1994). In this method, a hybrid gene is made in which DNA encoding a peptide or protein domain of interest, such as a peptide containing a region of random sequences, is inserted at a site in the middle portion of the gene encoding the minor coat protein, pIII, of bacteriophage fd. When expressed in the bacteriophage, the portion of the resulting fusion protein containing the peptide of interest is present at the tip of the phage capsid. Phage that thus display the peptide of interest can then be used in selection methods for, e.g., identifying fusion proteins that contain regions that bind to specific DNA probes or antibodies. Selected phage can be amplified and sequence analysis of the selected random sequences can then be carried out. For use in isolating δ-EKLFs, the phage display method is carried out as follows.

Amino acid positions −1 and 2–6 are randomized in each of the three β-EKLF zinc fingers (see FIG. 2; also see Miller et al., Mol. Cell. Biol. 13(5):2776 for the nucleotide and amino acid sequences of β-EKLF), and variants that specifically bind nucleic acids containing δ-globin promoter sequences (e.g., 5'-TGA AAC CCT-3' or 5'-CTA ATG AAA-3') are selected. Because of limitations of the phage display method, preferably, one zinc finger is randomized and selected at a time. For example, beginning with the first β-EKLF zinc finger (see FIG. 2), overlapping oligonucleotides spanning the coding region of the zinc finger, and containing all four bases at the positions corresponding to amino acids −1 and 2–6, are annealed and extended with DNA polymerase (e.g, Sequenase 2.0, United States Biochemical) to create a library of DNA fragments that encode a mixture of all possible amino acid combinations at amino acid positions −1 and 2–6. These fragments are linked to the second and third zinc fingers of β-EKLF, and cloned into the vector fUSE5 (Smith et al., Meth. Enz. 217:228, 1993). The resulting random library is then transformed into an appropriate *E. Coli* strain, such as MC1061 (Smith et al., Methods Enzymol. 217:228, 1993), and a collection of bacteriophage are produced, which express a modified β-EKLF in their coat protein. In these modified β-EKLFs, the first zinc finger contains random sequences in amino acid positions −1 and 2–6, and the second and third zinc fingers are wild type.

Phage that display the modified β-EKLFs are then mixed with biotin-labeled double-stranded DNA fragments containing a modified β-EKLF binding site. Because the zinc fingers are being selected one at a time, the modified β-EKLF binding site has only one of the triplets modified. For example, in selecting the first zinc finger of δ-EKLF, the first triplet of the β-EKLF binding site is replaced with the corresponding δ-globin site. Thus, the DNA fragment contains 5'-CTA CAC CCT-3' instead of 5'-CCA CAC CCT-3', or 5'-TGA CTA GGG-3' instead of 5'-ACC CTA GGG-3'. Phage containing sequences that bind to the DNA probes can be detected by contacting the phage/DNA probe mixtures with streptavidin using, e.g., a biopanning method (see, e.g., Rebar et al., Science 263:671, 1994).

Once the first zinc finger of a modified β-EKLF variant is selected which binds to the first δ-EKLF binding site triplet, then the above-described methods are repeated to select second and third zinc fingers, which bind to the second and third δ-EKLF binding site triplets. When all three β-EKLF zinc fingers have been modified so that they each bind to their respective δ-EKLF binding site triplets, the DNA that encodes them is linked to the remainder of the β-EKLF protein coding sequence, to produce a nucleic acid encoding a δ-EKLF.

In addition to phage display, other methods known in the art for selecting modified zinc fingers from libraries including random sequences can be used for isolating δ-EKLFs. For example, the challenge phage, method can be used. Other standard methods are described, e.g., by Ausubel et al. (*Current Protocols in Molecular Biology*, John Wiley & Sons, New York, 1994).

Expression of δ-EKLF in Hematopoietic Stem Cells

Expression of δ-EKLF in erythrocyte precursor cells (e.g., erythrocyte burst-forming cells (BFC-E) and erythrocyte colony-forming cells (CFC-E)) and erythrocytes can be used to increase δ-globin production, and thus RbA$_2$ levels, in these cells and their progeny. In order to accomplish this, a gene encoding a δ-EKLF polypeptide can be introduced into hematopoietic stem cells, or erythrocyte precursor cells (e.g., BFC-E and CFC-E), using gene therapy methods known in the art. Preferably, δ-EKLF genes are stably introduced into hematopoietic stem cells, which are capable of self renewal, in order to minimize the number of treatments required. Any vectors that can be used to accomplish stable integration, such as adeno-associated viral (AAV) vectors and retroviral vectors (e.g., moloney murine leukemia viral vectors), can be used. Use of an AAV vector for introduction of a gene, such as a gene encoding a δ-EKLF polypeptide, into hematopoietic stem cells can be carried out as follows. This method is also described by Luhovy et al. (Biology of Blood and Marrow Transplantation 2:24–30, 1996).

AAV belongs to the genus Dependovirus (family parvoviridae), and is also known as adenosatellite and dependovirus. These viruses are antigenically unrelated to adenovirus, but require the presence of adenovirus in order to replicate. There are at least four serotypes of AAV, all of which share common antigens. Dependoviruses are characterized in that they (1) are small and contain single-stranded DNA, (2) have virions of 18 to 26 nm in diameter, (3) are not enveloped, (4) are ether-resistant, (5) have capsids with cubic symmetry (with 32 capsomeres), and (6) replicate and assemble into virions in the nucleus of infected cells. AAV vectors for use in gene therapy methods contain AAV inverted terminal repeats (ITRs).

Appropriate promoters and genes, such as genes encoding δ-EKLF polypeptides, are introduced into AAV vectors using standard methods in the art (see, e.g., Sambrook et al., eds., *Molecular Cloning: A Laboratory Manual*, 2nd Edition, Cold Spring Harbor Laboratory, Cold Spring Harbor, N.Y., 1989). Any promoter that is sufficient to direct initiation of transcription in a hematopoietic cell, such as a hematopoietic stem cell or an erythrocyte precursor cell, can be used in the invention. For example, a preferred non-tissue specific promoter is the cytomegalovirus (CMV) promoter (DeBernardi et al., Proc. Natl. Acad. Sci. USA 88:9257–9261, 1991, and references therein). Any appropriate hematopoietic cell-type specific promoter may also be used in the invention. For example, globin promoters, such as the β-globin promoter (Karlsson et al., Ann. Rev. Biochem. 54:1071–1108, 1985, and references therein) (e.g., a β-globin promoter including a DNAse hypersensitivity site, such as HS2), may be used.

The hematopoietic stem cells can be obtained from any appropriate source. Preferably, the cells are obtained from the patient into which they are to be transplanted after AAV-infection. Hemnatopoietic stem cells are obtained from patients and, after infection by AAV vectors, are introduced back into patients using standard methods in the art (see, e.g., U.S. Pat. No. 5,061,620; Rubenstein et al., (eds.) Scientific American Medicine, Scientific American, Inc. (New York, 1978), and references therein).

Production of AAV vectors containing genes encoding δ-EKLF polypeptides can be carried out using the semi-packaging cell line and vectors described below.

Production of High Titer, Recombinant AAV

A packaging cell line can be used to produce a high titer ($10^7$–$10^8$ pfu/ml) stock of AAV-derived vectors containing genes encoding a δ-EKLF polypeptide (e.g., a δ-EKLF gene functionally linked to a CMV promoter). Such a "semi-packaging" cell line can be established with a silent episomal vector, such as pEBAVrc. This vector contains an EBV replication origin and an EBNA1 gene. This arrangement enables the vector to be established as an episome and to replicate to high copy numbers. The rep-cap genes of AAV are inserted into the vector with their natural control elements, so these genes are activated only in the presence of adenovirus early gene products. This arrangement provides a switch-system to regulate the expression of the rep gene, which has been found to have a cytostatic effect. The vector also contains a hygromycin resistance gene to enable selection for cells that contain the vector. The plasmid sequences of the vector contain an ampicillin resistance gene and a bacterial replication origin for replicating the DNA in bacteria.

An AAV vector containing a δ-EKLF gene can be made in a similar vector, to generate pEBAVcmv/δEKLF. This vector contains a CMV immediate-early transcriptional cassette containing a δ-EKLF gene, which is flanked by the two ITR sequences of AAV.

To establish the semi-packaging cell line, HeLa cells in 100 mm culture dishes are transfected with pEBAVrc. HeLa cells are seeded 24 hours prior to transfection, and are allowed to reach 50–70% confluence at the time of transfection. Cells are washed once with serum-free DMEM (Gibco, Gaithersburg, Md.). After removal of the medium, 8 ml of DMEM containing 10% fetal calf serum is added to the culture on the next day. At 12 hours after this medium change, cells are treated with trypsin and passed to three 100 mm dishes in DMEM containing 10% fetal calf serum and 270 u/ml of Hygromcyin (Sigma). Special care should be taken to allow cells to settle at the bottom of the plate individually. Cells are selected with hygromycin for 10 to 15 days, or until individual colonies begin to grow. Colonies from 3 to 4 dishes are treated with trypsin and pooled into one 100 mm dish. Cells are kept at 60–70% confluence in medium containing 200 u/ml hygromycin. When 90% confluence is reached, cells are transferred into four 100 mm dishes in DMEM containing 10% DMEM without hygromycin. At 24 hours post-seeding, each 100 mm dish of cells is transfected with 5 μg each of pEBAVrc and pEBAVcmv/δ-EKLF. At 3 hours after the addition of the transfection medium, wild-type adenovirus (HuAd5) is added to the cells at an MOI of 10, without removal of the transfection medium. At 12 hours after the transfection, the medium is changed to DMEM containing 5% fetal calf serum and incubated for three days, or until most of the cells show cytopathic effects. All of the media, except 1 ml, is removed from each 100 mm dish. Cells are then scraped off the plate and transferred into a 10 ml screw-cap tube. This viral lysate is stored at −100° C., until further treatment.

The viral lysate is thawed on ice, and sonicated for 10–15 minutes with pulse ultrasound. The tube is put back on ice periodically to prevent the sample from heating up. The viral lysate is then spun at 15,000 rpm for 10 minutes in a JL-20 centrifuge (Beckman). The supernatant is removed and aliquoted into freezing wells of 10 ml each and stored at −100° C. For infecting hematopoietic stem cells, it is not necessary to remove or inactivate the adenovirus, since stem cells lack receptors for adenovirus. For infection of cells that are susceptible to adenovirus infection, adenovirus should be removed by chromatography or by CsCl gradient centrifugation.

The titer of the virus can be determined by the rate of transduction of HeLa cells with the δ-EKLF gene. One, two, and three ml of the viral stock can be used to infect HeLa cells in 24-well plates. At 24 hours post-infection, the cells can be fixed with 0.1% glutaraldehyde at 4° C. for 2 minutes, and washed thoroughly with DMEM. Cells can then be monitored for δ-EKLF expression, using standard methods. The transfection procedure is as follows. For each 100 mm dish, 8–10 μg DNA is dissolved in 2 ml of DMEM or transfection medium from BRL. 90–100 μl of lipofectamine (BRL) is suspended in 2 ml of DMEM. The lipid containing medium is mixed with the DNA containing medium slowly and dropwise, while the tube is gently rotated. After mixing well by gently rotating the tube, the transfection mixture is incubated for 30 minutes at room temperature. The mixture is then diluted with DMEM to a total volume of 8 ml. The mixture is then added to the cells, which had been washed once or twice with DMEM without serum. Care should be taken to not allow the cells to dry between each wash.

Purification of Human Hematopoietic Stem Cells

Bone marrow is obtained from individuals following an IRB approved protocol. Mononuclear cells are purified using density gradient centrifugation using standard procedures. The mononuclear bone marrow cells are isolated by Ficoll/Hypaque density gradient centrifugation (average yield $1-2 \times 10^8$ cells). The use of magnetic activated cell sorting (MACS) allows for rapid enrichment of CD34+ cells (Kato and Radbruch, Cytometry 14:384–392, 1993). The cells are labeled with anti-CD34+ antibodies conjugated with magnetic particles, and run through the magnetic separation column from Miltenyi Biotec (Sunnyvale, Calif.). Hematopoietic stem cells can be further enriched by selecting for and against various surface molecules according to principles outlined by Baum et al. (Proc. Natl. Acad. Sci. USA 89:2804–2808, 1992). The progenitors can be labeled with an FITC conjugated antibody that recognizes a different CD34+ epitope than the magnetic bead conjugated anti-CD34 antibody. Lin- cells are isolated by a negative selection using a cocktail of PE labeled antibodies that recognize myeloid, B cells, T cells, and NK cell markers (CD 2, CD 14, CD 19, CD 56). Thy+ cells are isolated by positive selection with biotinylated, anti-human Thy mouse monoclonal antibody that was labeled with streptavidin-conjugated, Texas red dye.

Infection of Hematopoietic Stem Cells

Ten thousand CD34+, Lin-, and Thy+ cells are suspended in 200 μl of DMEM without serum and are dispensed into a single well of a 96 well plate. Ten microliters of the recombinant virus (AAV cmv/δ-EKLF; $10^8$ u/ml) are then added to the cells and incubated at 37° C. for 16 hours. The cells are then washed 3 times with DMEM without serum and can be plated into long term culture as described by Eaves et al. (J. Tiss. Cult. Meth. 13:55–62, 1991) for further analysis.

Analysis of Cells Plated Into Long Term Culture

After 6 weeks in long term culture, cells are removed and plated in methylcellulose for clonogenic progenitor assays (Eaves and Eaves, Blood 52:1196–1210, 1978). BFU-E are picked after 14 days, DNA is extracted, and PCR is performed with primers specific for δ-EKLF. PCR products are run on agarose gels, blotted to nitrocellulose, and hybridized with radiolabeled, δ-EKLF sequences.

δ-EKLF Polypeptide Expression

δ-EKLF polypeptides can be used to produce antibodies against δ-EKLF. Such antibodies can be used to monitor the levels of expression of δ-EKLF in patients treated by the gene therapy methods of the invention. In general, δ-EKLF polypeptides can be produced by transformation of a suitable host cell with all or part of a δ-EKLF-encoding nucleic acid fragment (e.g., a cDNA fragment) in a suitable expression vehicle.

Those skilled in the field of molecular biology will understand that any of a wide variety of expression systems can be used to provide the recombinant protein. The precise host cell used is not critical to the invention. The δ-EKLF protein can be produced in a prokaryotic host (e.g., *E. coli*) or in a eukaryotic host (e.g., *Saccharomyces cerevisiae*, insect cells, e.g., Sf21 cells, or mammalian cells, e.g., COS-1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al. (supra); expression vehicles can be chosen from those provided, e.g., in *Cloning Vectors: A Laboratory Manual* (P.H. Pouwels et al., 1985, Supp. 1987).

One particular expression system is the baculovirus system (using, for example, the vector pBacPAK9) available from Clontech (Pal Alto, Calif.). Alternatively, a δ-EKLF polypeptide can be produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the δ-EKLF polypeptide is cloned into an expression vector which includes the dihydrofolate reductase (DHFR) gene. Integration of the plasmid and, therefore, the δ-EKLF polypeptide-encoding gene into the host cell chromosome is selected for by including 0.01–300 μM methotrexate in the cell culture medium (as described in Ausubel et al., supra). This type of dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

Once the recombinant δ-EKLF polypeptide is expressed, it can be isolated, e.g., using affinity chromatography. In one example, an anti-δ-EKLF polypeptide antibody (e.g., produced as described herein) can be attached to a column and used to isolate the δ-EKLF polypeptide. Lysis and fractionation of δ-EKLF polypeptide-harboring cells prior to affinity chromatography can be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short δ-EKLF polypeptide fragments (e.g., fragments containing zinc fingers), can also be produced by chemical synthesis (e.g., by the methods described in *Solid Phase Peptide Synthesis*, 2nd ed., 1984, The Pierce Chemical Co., Rockford, Ill.).

These general techniques of polypeptide expression and purification can also be used to produce and isolate useful δ-EKLF fragments (e.g., fragments containing one or more zinc fingers, or portions thereof) or analogs.

Antibodies against δ-EKLF

To generate δ-EKLF-specific antibodies, a δ-EKLF coding sequence (e.g., a sequence encoding a δ-EKLF zinc finger DNA binding domain) can be expressed as a C-terminal fusion with glutathione S-transferase (GST) (Smith et al., Gene 67:31–40, 1988). The fusion protein can be purified on glutathione-Sepharose beads, eluted with glutathione cleaved with thrombin (at a engineered cleavage site), and purified to the degree necessary for immunization of rabbits.

Primary immunizations can be carried out with Freund's complete adjuvant and subsequent immunizations with Freund's incomplete adjuvant. Antibody titers can be monitored by Western blot analysis and immunoprecipitation using the thrombin-cleaved δ-EKLF protein fragment of the GST-δ-EKLF fusion protein. Immune sera can be affinity purified using a CNBr-Sepharose-coupled δ-EKLF polypeptide. Antiserum specificity is determined using a panel of unrelated GST proteins.

As an alternate or adjunct immunogen to GST fusion proteins, peptides corresponding to relatively unique hydrophilic regions of δ-EKLF can be generated and coupled to keyhole limpet hemocyanin (KLH) through an introduced C-terminal lysine. Antiserum to each of these peptides can be similarly affinity purified on peptides conjugated to BSA, and specificity tested in ELISA and Western blots using peptide conjugates, and by Western blot and immunoprecipitation using δ-EKLF expressed as a GST fusion protein.

Alternatively, monoclonal antibodies can be prepared using δ-EKLF polypeptides and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In *Monoclonal Antibodies and T Cell Hybridomas*, Elsevier, N.Y., 1981; Ausubel et al., supra). Once produced, monoclonal antibodies can also be tested for specific δ-EKLF recognition by Western blot or immunoprecipitation analysis (e.g., by the methods described in is Ausubel et al., supra). Antibodies that specifically recognize δ-EKLF are considered to be useful in the invention; such antibodies can be used, e.g., in an immunoassay to monitor the level of δ-EKLF produced by a mammal (e.g., a human treated using a gene therapy method of the invention).

Preferably, antibodies of the invention are produced using fragments of the δ-EKLF polypeptide that appear likely to be antigenic, as determined by criteria such as high frequency of charged residues. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably, including at least three booster injections.

Insertion of a β-EKLF Binding Site Activates Transcription of the δ-Globin Promoter Experiments demonstrating that the presence of the β-EKLF binding site leads to activation of a downstream δ-globin promoter were carried out as follows.

Plasmid Constructions

The construction of plasmid HS2 β/Luciferase has been described (Donze et al., J. Biol. Chem. 270:1955, 1995). The plasmid contains the 1.5 kb KpnI-BglII human Locus Control Region HS2 fragment upstream of the −265 to +48 human β-promoter driving the Luciferase reporter gene of plasmid pGL2-Basic (Promega Corp.). HS2δ/Luciferase was constructed by PCR amplification of the −265 to +48 region of the δ-promoter with BglII ends attached to the primers. The template used was a human globin locus subclone containing the entire δ-gene, and the primer sequences (BglII sites underlined) were: upstream 5'-CTCGAGGCTAGC AGATCTGCAAAAATGAAACTAGA-3' (SEQ ID NO:1); downstream, 5'-CTCGAGGCTAGC AGATCTCTGTTGAGGTTGCTAGTGA-3' (SEQ ID NO:2). The PCR product was digested with BglII and cloned into the plasmid HS2/Luc (Caterina et al., Nucleic Acids Res. 22:2383, 1994). Modified $\delta^{CAC-1}$ and $\delta^{CAC-2}$ promoters were made by the megaprimer mutagenesis method (Sarkar et al., BioTechniques 8:404, 1990; Barik et al., BioTechniques 10:489, 1991; Aiyar et al., BioTechniques 14:366, 1993), using the same outside oligonucleotides listed above with the following mutagenic oligonucleotides: $\delta^{CAC-1}$, 5'-TTTTCATTCTCACAAACTAA CCACACCCTGCTTATCTTAAAC CA-3' (SEQ ID NO:3); $\delta^{CAC-2}$, 5'-TCATTTTTCATTCTCACAAAC ACCACACCCTCCCTGCTTATCTTAAACCAA-3' (SEQ ID NO:4). The consensus EKLF binding sites are underlined and in bold, and these fragments were cloned into HS2/Luc, as is described above.

To construct the HS2δ-β gene plasmids, the 3.0 kb XbaI-SphI fragment of the δ-globin gene (from −400 to about 1 kb downstream of the poly A site) was first subcloned into pUC19. The modified δ-promoters (amplified from the −400 XbaI site to the SalI site at −13) were then synthesized by megaprimer mutagenesis using the same mutagenic oligos listed above and outside primers 5'-AGTTTAAACTGCAGCAATAG-3' (SEQ ID NO:5) (starting at −460 of the δ-promoter), and 5'-CTTCTCCTCAGGAGTCAG-3' (SEQ ID NO:6), (just downstream of the translation start site). These PCR fragments were cut with XbaI and SalI, and used to replace the corresponding wild type fragment in the δ-gene pUC19 subclone. The $\delta^{GAL4}$-promoter was constructed in the same fashion, using the mutagenic oligonucleotide 5'-GAAGGTTCATTTTTCATTCT CCGGAGGACAGTCCTCCGGCTTATCTTAAACCAA CCTGC-3' (SEQ ID NO:7), with the consensus GAL4 binding site (Giniger et al., Cell 40:767, 1985) underlined and in bold. Each of these δ-genes was cut out of the pUC19 vector with XbaI and HindIII, blunted with S1 nuclease, and cloned into plasmid 5'HS2 (K-P) $\beta^{22}$ (Caterina et al., Nucleic Acid Res. 22:1006, 1994), which was cut with ClaI and blunted with S1 nuclease. All PCR amplified regions in each of these constructs were completely verified by dideoxy sequencing using the Sequenase kit (United States Biochemical).

The pCIneoGAL4$_{(1-147)}$/EKLF plasmid was constructed in two steps: A 0.8 kb NcoI-MslI cDNA fragment containing the coding sequence (amino acids 2–275) of the murine EKLF activation domain (from plasmid pSG5-EKLF (Miller et al., Mol. Cell. Biol. 13:2776, 1993)) was blunted with S1 nuclease and cloned in frame into the GAL4 DNA binding domain expression plasmid pBXG1. The pBXG1/EKLF plasmid was cut with HindIII and BamHI, the 1.3 kb GAL4$_{(1-147)}$/EKLF fragment was isolated, blunted with S1 nuclease, and cloned into pCIneo (Promega Corp.) cut with SmaI. As a control, the 0.5 kb GAL4 binding domain HindIII-BamHI fragment from pBXG1 was cloned into pCIneo, as is described above (pCIneo-GAL4$_{(1-114)}$).

Mouse Erythroleukemia (MEL) Cell Transfections

MEL cells were maintained in DMEM containing 10% fetal bovine serum. For transient transfections, cells were washed once and resuspended to $10^8$ cells/ml in RPMI 1640 medium without serum. For transient luciferase assays, 40 µg of HS2 promoter/Luciferase plasmids were mixed with 5 µg internal control plasmid CMV-βgal (Clontech) in 100 µl phosphate buffered saline (PBS) and placed in a 0.4 cm gap electroporation cuvette (Bio-Rad). $5 \times 10^7$ MEL cells in 0.5 ml RPMI 1640 medium (without serum) were added to each cuvette, and the cells were electroporated at 260 V and 960, µF in a Bio-Rad Gene Pulser. The contents of each cuvette were transferred into a 100 mm plate containing 10 ml DMEM/10% FBS, and incubated for 8 hours. After 8 hours, DMSO was added to 1.65% to induce erythroid differentiation. This 8 hour pre-incubation, before DMSO induction, increased cell viability and gene expression levels several fold when compared to cells induced immediately after electroporation. Cultures were incubated for three days and then cell extracts were assayed for luciferase and β-galactosidase as described (Caterina et al., Nucleic Acids Res. 22:2383, 1994; Donze et al., J. Biol. Chem. 270:1955, 1995). Transient transfections were performed three times in triplicate.

Transfection of MEL cells to produce G418 resistant populations was performed essentially as described by Collis et al. (EMBO J. 9:233, 1990). Twenty micrograms of HS2 δ–β plasmids (with δ, $δ^{CAC-1}$, or $δ^{CAC-2}$ promoters) were mixed with a 1/10 molar ratio of plasmid pgk-neo (the murine phosphoglycerate kinase promoter driving neomycin phosphotransferase). Both plasmids were linearized with KpnI, precipitated, and dissolved in 100 µl PBS. The plasmid mix was placed into a 0.4 cm electroporation cuvette, and $2 \times 10^7$ MEL cells (prepared as is described above) in 0.5 ml were added. Cells were electroporated at 200 V is and 960 µF, and transferred to 30 ml DMEM/10% FBS in a 75 cm² culture flask. After 48 hours, G418 was added to a final concentration of 300 µg/ml, and resistant cell populations were selected for two weeks. Cells were then induced with 1.65% DMSO for three days, and total RNA was extracted as described (Chomczynski et al., Anal. Biochem. 162:156, 1987). The HS2 $δ^{GAL4}$–β experiments were performed as above, using a 1:10 molar ratio of the pCIneo plasmids, which were linearized with XmnI.

Analysis of Relative Levels of δ- and β-transcripts

The relative levels of δ to β-globin transcripts were determined by the Single Nucleotide Primer Extension (SNuPE) assay, which is based on detecting single known nucleotide differences in allelic RNAs (Szabo et al., Genes Dev. 9:1857, 1995). Briefly, RNA from MEL cells transfected with HS2 δ–β constructs was amplified by RT-PCR (cDNA cycle kit, Invitrogen) using oligo dT to prime the cDNA reaction. The PCR primers were: upstream, 5'-TGTTCACTAGCAA CCTCAAAC-3' (SEQ ID NO:8); and downstream, 5'-TGAAGTTCTCAGGAT CCACGT-3' (SEQ ID NO:9). There are no differences in the δ- and β-globin sequences in these regions and the primers do not amplify mouse globin mRNAs. These oligos specifically amplify corresponding 341 bp fragments of both the human δ- and β-globin cDNAs, and the fragments were purified by agarose gel electrophoresis. The detection oligo, 5'-CTTCTCCTCAGGAGTCAG-3' (SEQ ID NO:6), hybridizes to identical sense strand sequences of both δ- and β-globin cDNA PCR products (corresponding to nucleotides +77 to +60 of each message), and is extended to base +59 by $α^{32}$P-dATP in the δ reaction or by $α^{32}$P-dGTP for the β reaction. Labeled products were resolved on a 15% polyacrylamide/8M urea gel, and bands were quantitated on a Molecular Dynamics Model 425 Phosphorimager. Linearity of the assay was verified as described (Szabo et al., Genes Dev. 9:1857, 1995) by mixing experiments using RNA from MEL cells transfected with either HS2 β or HS2 β-promoter/ δ-gene as sources containing the individual messages.

EXPERIMENTAL RESULTS

To test the feasibility of using a modified EKLF to activate δ-globin gene expression, we determined whether a δ-globin promoter containing a β-globin EKLF binding site would increase expression by recruiting endogenous cellular β-EKLF in transient transfection assays. We replaced the defective β-EKLF binding site in the δ-globin promoter (TGAAACCCT from −89 to −81, FIG. 1B) with the consensus CCACACCCT, to construct the plasmid HS2 $δ^{CAC-1}$/Luciferase. We also constructed a modified δ-globin promoter that contained the CCACACCCT sequence at −93 to −85, so that the β-EKLF binding site would be positioned the same distance from the transcription start site as it is in the β-globin promoter (HS2 $δ^{CAC-2}$/Luciferase).

Figure 3A:
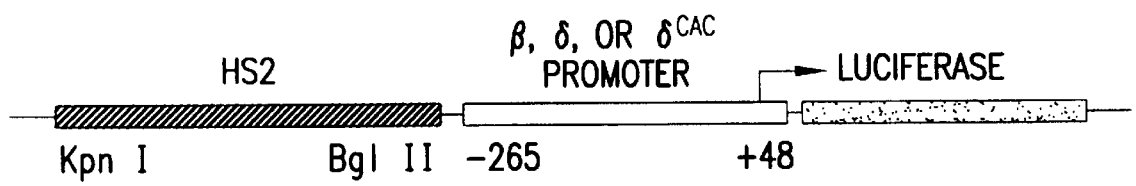
FIG. 3A is a schematic representation of δ-globin promoter/reporter plasmids. The 1.5 kb KpnI-BglII LCR HS2 fragment was linked to the −265 to +48 wild type β-, δ-, and modified δ-globin promoters described in the above description of FIG. 1B. These promoters were used to drive luciferase reporter gene expression in transiently transfected MEL cells. Luciferase activity was normalized to β-galactosidase expression from an internal control CMV-β-galactosidase plasmid.
Figure 3B:
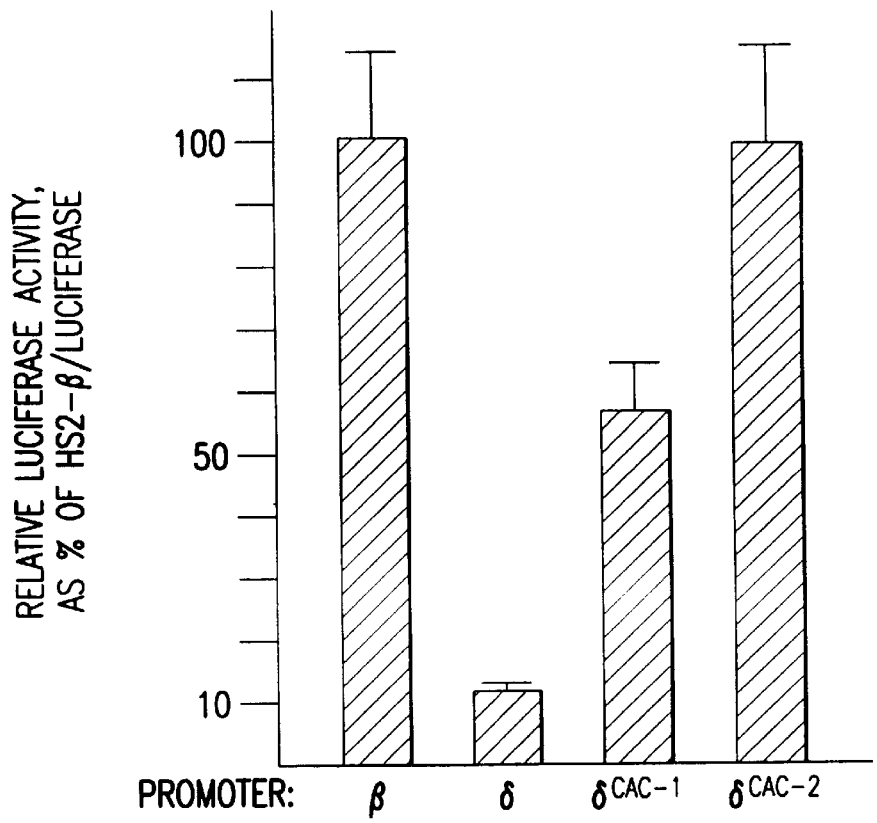
FIG. 3B is a graph showing the results of transient expression of HS2δ-promoter/Luciferase plasmids in mouse erythroleukemia (MEL) cells. HS2 β/Luc expression was normalized to 100%. Inclusion of the consensus β-EKLF binding site in the $\delta^{CAC-1}$ and $\delta^{CAC-2}$ promoters increased HS2 δ/Luc expression from 10% to 56% and 99% of HS2 β/Luc, respectively.

FIG. 3B illustrates the relative expression levels of these modified δ-promoter/Luciferase reporter constructs (FIG. 3A) when linked to a Locus Control Region HS2 fragment and transiently transfected into mouse erythroleukemia (MEL) cells. In this assay, HS2 δ/Luc was expressed at 10% of the level of HS2 β/Luc. When the consensus β-EKLF site was placed in the δ-globin promoter at the −81 to −89 site (HS2 $δ^{CAC-1}$/Luc), expression was increased approximately 5 fold, to 56% of HS2 β/Luc expression. HS2 $β^{CAC-2}$/Luc, with the consensus β-EKLF site at −85 to −93, expressed the reporter gene at 99% of HS2 β/Luc. These results demonstrate that the major defect of the δ-globin gene proximal promoter is the lack of a consensus β-EKLF binding site.

Figure 4A:
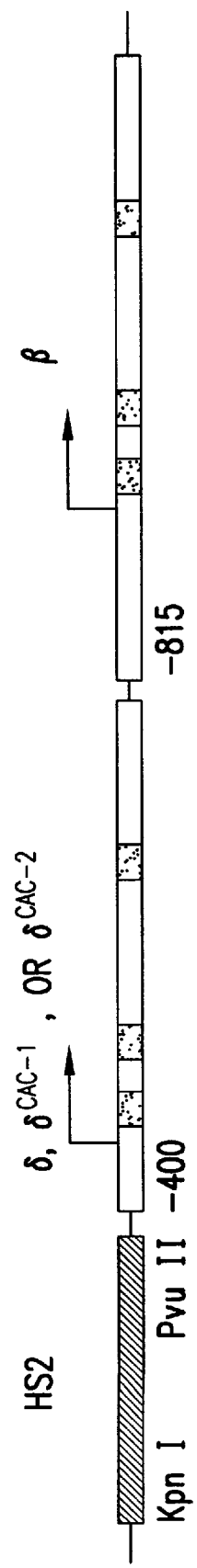
FIG. 4A is a schematic representation of HS2 δ−β constructs. The parental HS2 δ−β construct contained a 1.9 kb KpnI-PvuII HS2 fragment, a 3.0 kb δ-globin gene fragment beginning at nucleotide −400 from the transcription start site, and a 2.1 kb β-globin gene fragment beginning at base −815 from the transcription start site. The corresponding $\delta_{CAC-1}$ and $\delta^{-CAC-2}$ modifications were inserted to create HS2 $\delta_{CAC-1}$-β and HS2 $\delta_{CAC-2}$-β. These constructs were transfected into MEL cells with a pgk-neo selectable marker and G418 resistant populations were selected. The cells were induced to differentiate with DMSO, and RNA was extracted for analysis.
Figure 4B:
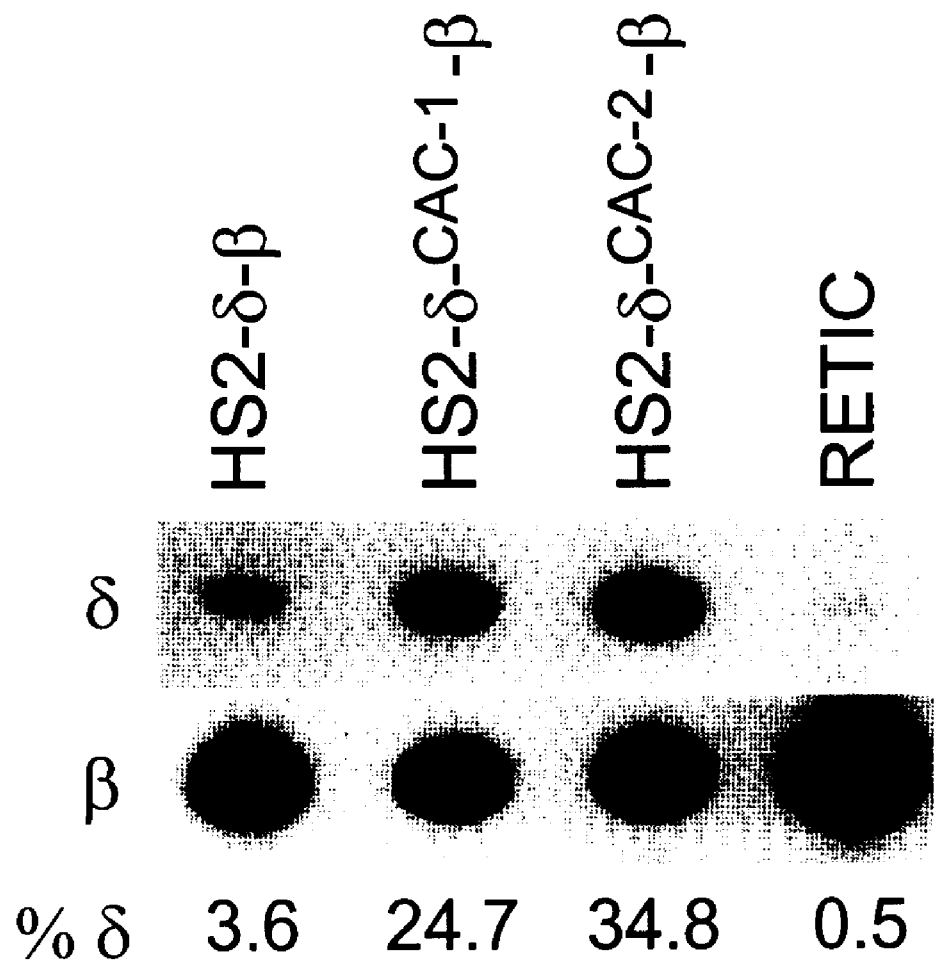
FIG. 4B is a photograph of denaturing gel analysis of the expression of modified δ-globin genes in MEL cells stably transfected with HS2 δ−β constructs. The relative levels of δ- and β-globin mRNAs were determined by the Single Nucleotide Primer Extension (SNuPE) assay (Szabo et al., Genes Dev. 9:1857, 1995) and quantitated by phosphorimage analysis. Inclusion of the consensus β-EKLF binding site in the $\delta_{CAC-1}$ and $\delta^{-CAC-2}$ globin genes increased δ-globin mRNA levels from 3.6% to 24.7% and 34.8% of total δ+β mNRA, respectively.

In addition to promoter defects, low δ-globin expression has been attributed to other differences between the δ- and β-globin genes. The δ-gene lacks intragenic enhancers, which augment β-globin expression (Kosche et al., Nucleic Acids Res. 13:7781, 1985; Behringer et al., Proc. Natl. Acad. Sci. USA 84:7056, 1987), and δ-globin mRNA is less stable than β-globin mRNA (Ross et al., J. Mol. Biol. 167:607, 1983). To assess the effects of these differences on $δ^{CAC-1}$ and $δ^{CAC-2}$ expression, we constructed complete δ-globin genes (see methods) containing the δ, $δ^{CAC-1}$, and $δ^{CAC-2}$ promoters (FIG. 4A). These δ-globin genes were used to produce HS2 δ–β constructs. The plasmids were then co-transfected into MEL cells with a pgk-neo selectable marker and G418 resistant populations were selected. After differentiation was induced with DMSO, RNA was extracted and the relative levels of δ- and β-globin mRNAs were determined by the Single Nucleotide Primer Extension assay (SNuPE) (Szabo et al., Genes Dev. 9:1857, 1995). Table 1 shows the results of these experiments. The level of δ-globin mNRA (δ/δ+β) in MEL cells was 3.0±1.3% for HS2 δ–β, 14.9±7.4% for HS2 $δ^{CAC-1}$–β, and 22.0±9.0% for HS2 $δ^{CAC-2}$–β. These results demonstrate that insertion of a consensus β-EKLF binding site in the δ-globin promoter significantly enhances δ-globin gene expression in a construct that contains the entire δ-globin gene. A representative example of the SNuPE assay is illustrated in FIG. 4B; δ/δ+β-globin mNRA in this experiment was 3.6% for HS2 δ–β, 24.7% for HS2 $δ^{CAC-1}$–β, and 34.8% for HS2 $δ^{CAC-2}$–β. As a control, δ- and β-globin mRNA levels were determined for human reticulocyte RNA (FIG. 4B); the δ/δ+β level was 0.6±0.2%.

Figure 5A:
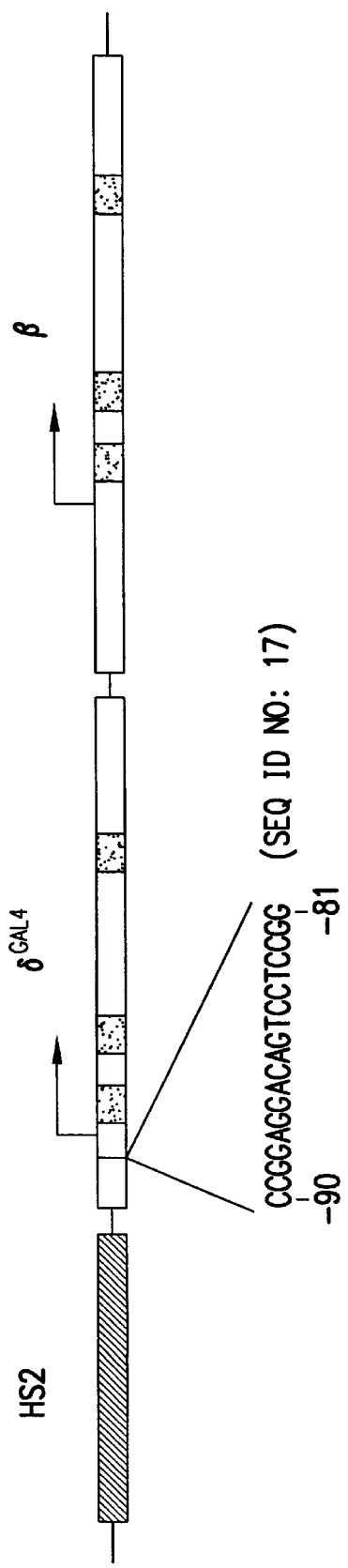
FIG. 5A is a schematic representation of the reporter plasmid HS2 $\delta^{-GAL4}$-β. This construct contains a consensus GAL4 binding site (expanded; SEQ ID NO:17), replacing δ-globin promoter nucleotides −80 to −99.
Figure 5B:
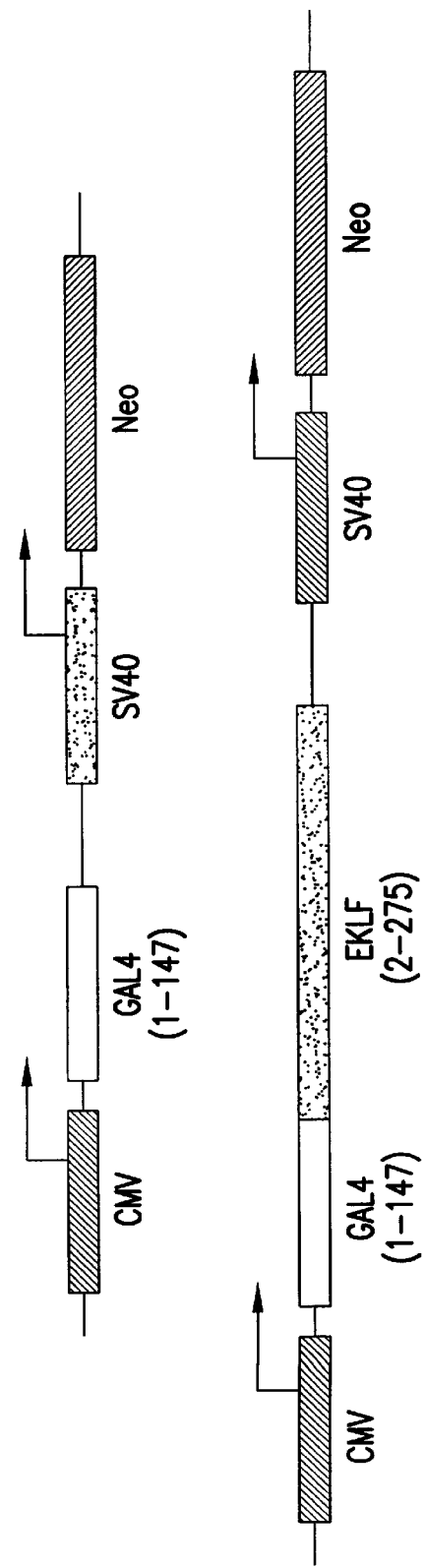
FIG. 5B is a schematic representation of pCIneo effector constructs expressing either the GAL4 DNA binding domain (amino acids 1-147) alone or $GAL4_{(1-147)}$ fused to the β-EKLF activation domain (amino acids 2-275).

These results show that β-EKLF binding to the δ-globin gene promoter significantly stimulates expression; however, the experiments do not exclude the possibility that other CACCC binding factors are responsible for this increase. To confirm that the β-EKLF activation domain can enhance δ-globin gene expression, we constructed an HS2 $\delta^{GAL4}$-β plasmid in which the consensus GAL4 binding site replaced sequences from −80 to −99 of the δ-globin gene promoter (FIG. 5A). The coding sequence of the murine β-EKLF activation domain (amino acids 2–275) was fused in frame to the GAL4 DNA binding domain (amino acids 1–147), and the fusion fragment was subcloned into the pCIneo expression vector (FIG. 5B). MEL cells were co-transfected with HS2 $\delta^{GAL4}$-β plus pCIneo-GAL4$_{(1-147)}$ or HS2 $\delta^{GAL4}$-β plus pCIneo-GAL4$_{(1-147)}$/β-EKLF. Stable pools of G418 resistant cells were selected and, after DMSO induction, δ- and β-globin mRNA levels were determined by the SNuPE assay described above.

Figure 5C:
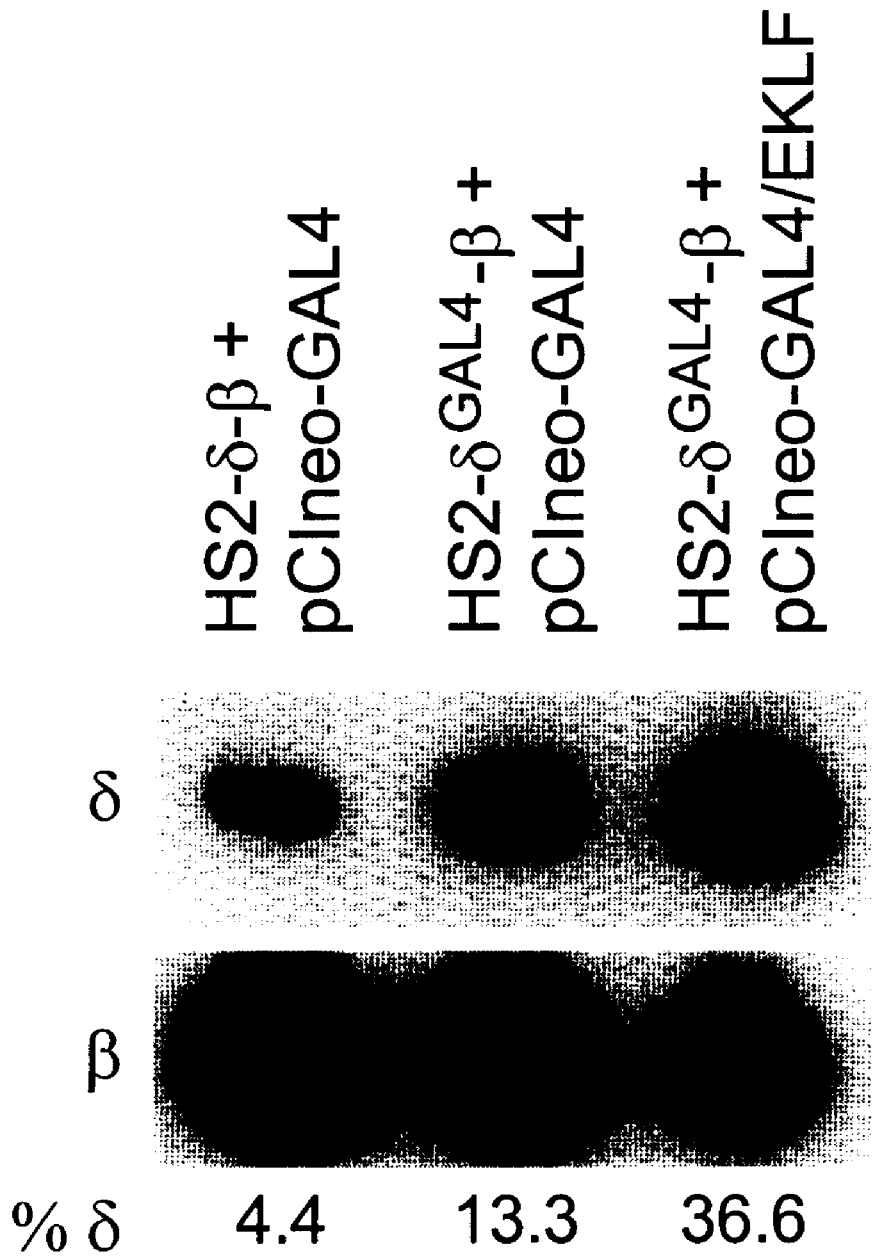
FIG. 5C is a photograph of denaturing gel analysis showing that GAL4/β-EKLF activates δ-globin gene expression in an HS2 $\delta^{GAL4}$-β construct. HS2 $\delta^{GAL4}$-β was stably transfected into MEL cells with either pCIneo-GAL4$_{(1-147)}$ or pCIneo-GAL4$_{(1-147)}$/β-EKLF, and relative transcript levels were determined by the SNuPE assay. The level of human δ/δ+ was 4.4% in cells containing HS2 δ−β, 13.3% in cells containing HS2 $\delta^{GAL4}$-β plus pCIneo-GAL4$_{(1-147)}$/β-EKLF. These results demonstrate that a modified β-EKLF can significantly increase δ-globin gene expression.

The data in Table 2 demonstrate that the level of human δ/δ+β mNRA is 9.9±2.5% in cells containing HS2 $\delta^{GAL4}$-β plus pCIneo-GAL4$_{(1-147)}$ and 27.8±7.1% in cells containing HS2 $\delta^{GAL4}$-β plus pCIneo-GAL4$_{(1-147)}$/β-EKLF. A representative example is illustrated in FIG. 5C; the level of human δ/δ+β mNRA is 4.4% in cells containing HS2 δ-β plus pCIneo-GAL4$_{(1-147)}$, 13.3% in cells containing HS2 $\delta^{GAL4}$-β plus pCIneo-GAL4$_{(1-147)}$, and 36.6% in cells containing HS2 $\delta^{GAL4}$-β plus pCIneo-GAL4$_{(1-147)}$/β-EKLF. These results demonstrate that a modified β-EKLF can significantly increase δ-globin gene expression.

The 3-fold increase (4.4% to 13.3%) of δ-globin gene expression observed when δ promoter sequences from −80 to −99 are replaced with a GAL4 binding site suggests that this region binds a factor that represses expression. A 3-fold increase is also observed when the −80 to −99 region of the δ-globin promoter is deleted in an HS2 δ-β globin construct.

TABLE 1

Relative Levels of δ-globin Transcripts From MEL Transfections and Human Reticulocyte Samples as % of Total Human δ + β Transcripts.

|  | HS2 δ-β | HS2 $\delta^{CAC-1}$-β | HS2 $\delta^{CAC-2}$-β | Reticulocyte |
|---|---|---|---|---|
| Exp. 1 | 3.6 | 24.7 | 34.8 | 0.5 |
| Exp. 2 | 1.9 | 10.0 | 15.0 | 0.7 |
| Exp. 3 | 1.6 | 5.8 | 12.3 | 0.8 |
| Exp. 4 | 4.7 | 19.0 | 25.7 | 0.3 |
| Avg. | 3.0 +/− 1.3 | 14.9 +/− 7.4 | 22.0 +/− 9.0 | 0.6 +/− 0.2 |

Expression of modified δ-globin genes in MEL cells stably transfected with HS2 δ-β constructs. These constructs were transfected into MEL cells with a pgk-neo selectable marker, and G418 resistant populations were selected. The cells were induced to differentiate with DMSO, and RNA was extracted for analysis. the relative levels of δ- and β-globin mRNAs were determined by the Single Nucleotide Primer Exteasion (SNuPE) assay and quantitated by phosphorimager analysis.

TABLE 2

Relative Levels of δ-globin Transcripts From MEL Cells Transfected with HS2-$\delta^{GAL4}$-β and GAL4$_{(1-147)}$ Expression Constructs as % of Total δ + β Transcripts

|  | HS2 $\delta^{GAL4}$-β + GAL4$_{(1-147)}$ | HS2 $\delta^{GAL4}$-β + GAL4$_{(1-147)}$/β-EKLF |
|---|---|---|
| Exp. 1 | 13.3 | 36.6 |
| Exp. 2 | 8.4 | 30.2 |
| Exp. 3 | 6.7 | 16.8 |
| Exp. 4 | 11.3 | 27.3 |
| Avg. | 9.9 +/− 2.5 | 27.8 +/− 7.1 |

GAL4/β-EKLF activates δ-globin gene expression in an HS2 δGAL4-β construct. HS2 δGAL-β was stably transfected into MEL cells with either pCIneo-GAL4$_{(1-147)}$ or pCIneo-GAL4$_{(1-147)}$/β-EKLF, and relative transcript levels were determined by the SNuPE assay. These results demonstrate that a modified β-EKLF can significantly increase δ-globin gene expression.

All publications referred to herein are incorporated by reference in their entirety. Other embodiments are in the following claims.

What is claimed is:

1. A nucleic acid molecule encoding a δ-EKLF polypeptide having the amino acid sequence of a β-EKLF polypeptide that comprises a substitution in amino acid position −1, 2, 3, 4, 5, or 6 of a zinc finger of said β-EKLF polypeptide, wherein said δ-EKLF polypeptide binds to a mammalian δ-globin promoter.

2. A cell that contains a nucleic acid molecule encoding a δ-EKLF polypeptide having the amino acid sequence of a β-EKLF polypeptide that comprises a substitution in amino acid position −1, 2, 3, 4, 5, or 6 of a zinc finger of said β-EKLF polypeptide, wherein said δ-EKLF polypeptide binds to a mammalian δ-globin promoter.

3. The cell of claim 2, wherein said cell is a hematopoietic stem cell.

4. The cell of claim 2, wherein said cell is an eyfthrocyte precursor cell.

5. A vector containing a nucleic acid molecule encoding a δ-EKLF polypeptide having the amino acid sequence of a β-EKLF polypeptide that comprises a substitution in amino acid position −1, 2, 3, 4, 5, or 6 of a zinc finger of said β-EKLF polypeptide, wherein said δ-EKLF polypeptide binds to a mammalian δ-globin promoter.

6. The vector of claim 5, wherein said vector is an adeno-associated viral (AAV) vector.

7. The vector of claim 5, wherein said vector is a retroviral vector.

8. The nucleic acid molecule of claim 1, wherein the β-EKLF polypeptide has the sequence set forth in SEQ ID NO:21.

9. The cell of claim 2, wherein the β-EKLF polypeptide has the sequence set forth in SEQ ID NO:21.

10. The vector of claim 5, wherein the β-EKLF polypeptide has the sequence set forth in SEQ ID NO:21.

* * * * *

SEQUENCE LISTING

<160> NUMBER OF SEQ ID NOS: 21

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence:[\]mNote = synthetic construct

<400> SEQUENCE: 1
ctcgaggcta gcagatctgc aaaaatgaaa ctaga                35

<210> SEQ ID NO 2
<211> LENGTH: 38
<212> TYPE: DNA

```
<213> ORGANISM: Artificial Sequence
<220> FEATURE:
<223> OTHER INFORMATION: Description of Artificial Sequence:[\]mNote =
      synthetic construct

<400> SEQUENCE: 2
ctcgaggcta gcagatctct gtttgaggtt gctagtga                              38

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 3
ttttcattct cacaaactaa ccacaccctg cttatcttaa acca                       44

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 4
tcatttttca ttctcacaaa ccacaccctc cctgcttatc ttaaaccaa                  49

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 5
agtttaaact gcagcaatag                                                  20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 6
cttctcctca ggagtcag                                                    18

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 7
gaaggttcat ttttcattct ccggaggaca gtcctccggc ttatcttaaa ccaacctgc       59

<210> SEQ ID NO 8
<211> LENGTH: 21
<212> TYPE: DNA
<213> ORGANISM: Artificial Sequence
```

```
<220> FEATURE:
<223> OTHER INFORMATION: Description of Artificial Sequence:[\]mNote =
      synthetic construct

<400> SEQUENCE: 8
tgttcactag caacctcaaa c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 9
tgaagttctc aggatccacg t                                              21

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 10
tgtggagcca caccctaggg ttggccaatc tactccc                             37

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 11
tcacaaacta atgaaaccct gcttatctta aaccaac                             37

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 12
tcacaaacta accacaccct gcttatctta aaccaac                             37

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 13
tcacaaacca caccctccct gcttatctta aaccaac                             37

<210> SEQ ID NO 14
<211> LENGTH: 23
<212> TYPE: PRT
<213> ORGANISM: Artificial Sequence
<220> FEATURE:
```

<223> OTHER INFORMATION: Description of Artificial Sequence:[\]mNote =
      synthetic construct

<400> SEQUENCE: 14

Cys Gly His Glu Gly Cys Gly Lys Ser Tyr Ser Lys Ser Ser His Leu
 1               5                  10                  15

Lys Ala His Leu Arg Thr His
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 15

Cys Ser Trp Asp Gly Cys Asp Trp Arg Phe Ala Arg Ser Asp Glu Leu
 1               5                  10                  15

Thr Arg His Tyr Arg Lys His
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence:[\]mNote =
      synthetic construct

<400> SEQUENCE: 16

Cys Gly Leu Cys Gly Leu Cys Pro Arg Ala Phe Ser Arg Ser Asp His
 1               5                  10                  15

Leu Ala Leu His Met Lys Arg His
            20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 17
ccggaggaca gtcctccgg                                              19

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 18 tgaaaccct                                                          9

<210> SEQ ID NO 19
<211> LENGTH: 9
<212> TYPE: DNA
<213> ORGANISM: Artificial Sequence
<220> FEATURE:
<223> OTHER INFORMATION: Description of Artificial Sequence:[\]mNote =
      synthetic construct

<400> SEQUENCE: 19 ctaatgaaa                                                                              9

<210> SEQ ID NO 20
<211> LENGTH: 376
<212> TYPE: PRT
<213> ORGANISM: Murine Beta-EKLF
<220> FEATURE:
<223> OTHER INFORMATION: Description of Artificial Sequence:[\]mNote = synthetic construct

<400> SEQUENCE: 20

```
Met Arg Gln Lys Arg Glu Arg Arg Pro Glu Val Gln Gly Gly His Gln
 1               5                  10                  15

Pro Ala Met Ala Ser Ala Glu Thr Val Leu Pro Ser Ile Ser Thr Leu
             20                  25                  30

Thr Thr Leu Gly Gln Phe Leu Asp Thr Gln Glu Asp Phe Leu Lys Trp
         35                  40                  45

Trp Arg Ser Glu Glu Thr Gln Asp Leu Gly Pro Gly Pro Pro Asn Pro
 50                  55                  60

Thr Gly Pro Ser Leu His Val Ser Leu Lys Ser Glu Asp Pro Ser Gly
 65                  70                  75                  80

Glu Asp Asp Glu Arg Asp Val Thr Cys Ala Trp Asp Pro Asp Leu Phe
                 85                  90                  95

Leu Thr Asn Phe Pro Gly Ser Glu Ser Pro Gly Thr Ser Arg Thr Cys
             100                 105                 110

Ala Leu Ala Pro Ser Val Gly Pro Val Ala Gln Phe Glu Pro Pro Glu
         115                 120                 125

Ser Leu Gly Ala Tyr Ala Gly Gly Pro Gly Leu Val Thr Gly Pro Leu
     130                 135                 140

Gly Ser Glu Glu His Thr Ser Trp Ala His Pro Thr Pro Arg Pro Pro
145                 150                 155                 160

Ala Pro Glu Pro Phe Val Ala Pro Ala Leu Ala Pro Gly Leu Ala Pro
                 165                 170                 175

Lys Ala Gln Pro Ser Tyr Ser Asp Ser Arg Ala Gly Ser Val Gly Gly
             180                 185                 190

Phe Phe Pro Arg Ala Gly Leu Ala Val Pro Ala Ala Pro Gly Ala Pro
         195                 200                 205

Tyr Gly Leu Leu Ser Gly Tyr Pro Ala Leu Tyr Pro Ala Pro Gln Tyr
     210                 215                 220

Gln Gly His Phe Gln Leu Phe Arg Gly Leu Ala Ala Pro Ser Ala Gly
225                 230                 235                 240

Gly Thr Ala Pro Pro Ser Phe Leu Asn Cys Leu Gly Pro Gly Thr Val
                 245                 250                 255

Ala Thr Glu Leu Gly Ala Thr Ala Ile Ala Gly Asp Ala Gly Leu Ser
             260                 265                 270

Pro Gly Thr Ala Pro Pro Lys Arg Ser Arg Thr Leu Ala Pro Lys
         275                 280                 285

Arg Gln Ala Ala His Thr Cys Gly His Glu Gly Cys Gly Lys Ser Tyr
     290                 295                 300

Ser Lys Ser Ser His Leu Lys Ala His Leu Arg Thr His Thr Gly Glu
305                 310                 315                 320

Lys Pro Tyr Ala Cys Ser Trp Asp Gly Cys Asp Trp Arg Phe Ala Arg
                 325                 330                 335
```

```
Ser Asp Glu Leu Thr Arg His Tyr Arg Lys His Thr Gly His Arg Pro
        340                 345                 350

Phe Cys Cys Gly Leu Cys Pro Arg Ala Phe Ser Arg Ser Asp His Leu
        355                 360                 365

Ala Leu His Met Lys Arg His Leu
        370                 375

<210> SEQ ID NO 21
<211> LENGTH: 361
<212> TYPE: PRT
<213> ORGANISM: Human Beta-EKLF
<220> FEATURE:
<223> OTHER INFORMATION: Description of Artificial Sequence:[\]mNote =
      synthetic construct

<400> SEQUENCE: 21

Met Ala Thr Ala Glu Thr Ala Leu Pro Ser Ile Ser Thr Leu Thr Ala
1               5                   10                  15

Leu Gly Pro Phe Pro Asp Thr Gln Asp Phe Leu Lys Trp Trp Arg
            20                  25                  30

Ser Glu Glu Ala Gln Asp Met Gly Pro Gly Pro Asp Pro Thr Glu
        35                  40                  45

Pro Pro Leu His Val Lys Ser Glu Asp Gln Pro Gly Glu Glu Asp
    50                  55                  60

Asp Glu Arg Gly Ala Asp Ala Thr Trp Asp Leu Asp Leu Leu Thr
65                  70                  75                  80

Asn Phe Ser Gly Pro Glu Pro Gly Gly Ala Pro Gln Thr Cys Ala Leu
                85                  90                  95

Ala Pro Ser Glu Ala Ser Gly Ala Gln Tyr Pro Pro Pro Glu Thr
            100                 105                 110

Leu Gly Ala Tyr Ala Gly Gly Pro Gly Leu Val Ala Gly Leu Leu Gly
            115                 120                 125

Ser Glu Asp His Ser Gly Trp Val Arg Pro Ala Leu Arg Ala Arg Ala
    130                 135                 140

Pro Asp Ala Phe Val Gly Pro Ala Leu Ala Pro Ala Pro Ala Pro Glu
145                 150                 155                 160

Pro Lys Ala Leu Ala Leu Gln Pro Val Tyr Pro Gly Pro Gly Ala Gly
                165                 170                 175

Ser Ser Gly Gly Tyr Phe Pro Arg Thr Gly Leu Ser Val Pro Ala Ala
            180                 185                 190

Ser Gly Ala Pro Tyr Gly Leu Leu Ser Gly Tyr Pro Ala Met Tyr Pro
        195                 200                 205

Ala Pro Gln Tyr Gln Gly His Phe Gln Leu Phe Arg Gly Leu Gln Gly
    210                 215                 220

Pro Ala Pro Gly Pro Ala Thr Ser Pro Ser Phe Leu Ser Cys Leu Gly
225                 230                 235                 240

Pro Gly Thr Val Gly Thr Gly Leu Gly Gly Thr Ala Glu Asp Pro Gly
                245                 250                 255

Val Ile Ala Glu Thr Ala Pro Ser Lys Arg Gly Arg Arg Ser Trp Ala
            260                 265                 270

Arg Lys Arg Gln Ala Ala His Thr Cys Ala His Pro Gly Cys Gly Lys
        275                 280                 285

Ser Tyr Thr Lys Ser Ser His Leu Lys Ala His Leu Arg Thr His Thr
    290                 295                 300

Gly Glu Lys Pro Tyr Ala Cys Thr Trp Glu Gly Cys Gly Trp Arg Phe
305                 310                 315                 320
```

```
Ala Arg Ser Asp Glu Leu Thr Arg His Tyr Arg Lys His Thr Gln Arg
                325                 330                 335

Pro Phe Arg Cys Gln Leu Cys Pro Arg Ala Phe Ser Arg Ser Asp His
                340                 345                 350

Leu Ala Leu His Met Lys Arg His Leu
            355                 360
```